(12) United States Patent
Takei

(10) Patent No.: US 9,918,801 B2
(45) Date of Patent: Mar. 20, 2018

(54) TREATMENT DEVICE

(71) Applicant: OLYMPUS CORPORATION, Hachioji-shi, Tokyo (JP)

(72) Inventor: Yusuke Takei, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/171,772

(22) Filed: Jun. 2, 2016

(65) Prior Publication Data
US 2016/0270871 A1 Sep. 22, 2016

Related U.S. Application Data

(63) Continuation of application No. PCT/JP2015/053267, filed on Feb. 5, 2015.

(30) Foreign Application Priority Data

Feb. 12, 2014 (JP) .................................. 2014-024754

(51) Int. Cl.
| | | |
|---|---|---|
| A61B 34/00 | (2016.01) | |
| A61B 17/32 | (2006.01) | |
| A61B 18/14 | (2006.01) | |
| A61B 18/08 | (2006.01) | |
| A61B 17/29 | (2006.01) | |

(52) U.S. Cl.
CPC ...... *A61B 34/71* (2016.02); *A61B 17/320068* (2013.01); *A61B 17/320092* (2013.01); *A61B 18/085* (2013.01); *A61B 18/1445* (2013.01); *A61B 34/70* (2016.02); *A61B 2017/2927* (2013.01)

(58) Field of Classification Search
CPC . A61B 34/71; A61B 34/70; A61B 17/320092; A61B 18/085; A61B 18/1445
USPC ............................................................. 606/1
See application file for complete search history.

(56) References Cited

U.S. PATENT DOCUMENTS

| | | | |
|---|---|---|---|
| 5,381,943 A | 1/1995 | Allen et al. | |
| 5,632,433 A | 5/1997 | Grant et al. | |
| 5,702,408 A * | 12/1997 | Wales | A61B 17/07207 606/139 |

(Continued)

FOREIGN PATENT DOCUMENTS

| | | |
|---|---|---|
| EP | 592244 A2 | 4/1994 |
| EP | 1759652 A2 | 3/2007 |

(Continued)

OTHER PUBLICATIONS

May 12, 2015 International Search Report issued in PCT/JP2015/053267.

(Continued)

*Primary Examiner* — Gary Jackson
*Assistant Examiner* — Zahed Kabir
(74) *Attorney, Agent, or Firm* — Oliff PLC

(57) ABSTRACT

A treatment device rotates a second rotation portion by operating an operation element. The second rotation portion switches between a first rotation position and a second rotation position. A direction of the end effector relative to the distal end of the sheath is changed in the first rotation position. A position of the end effector relative to the distal end of the sheath is maintained in the second rotation position.

16 Claims, 13 Drawing Sheets

(56) References Cited

U.S. PATENT DOCUMENTS

| | | | |
|---|---|---|---|
| 5,782,859 A * | 7/1998 | Nicholas | A61B 17/0218 600/204 |
| 6,791,289 B1 * | 9/2004 | Long | F16H 27/06 318/443 |
| 2005/0006430 A1 * | 1/2005 | Wales | A61B 17/07207 227/175.1 |
| 2007/0049435 A1 | 3/2007 | Jinno et al. | |
| 2007/0287993 A1 | 12/2007 | Hinman et al. | |
| 2009/0031872 A1 * | 2/2009 | Lykam | A61J 3/06 83/78 |
| 2009/0198272 A1 | 8/2009 | Kerver et al. | |
| 2012/0074200 A1 | 3/2012 | Schmid et al. | |
| 2012/0078244 A1 * | 3/2012 | Worrell | A61B 17/07207 606/33 |
| 2012/0179215 A1 | 7/2012 | Soubeiran | |

FOREIGN PATENT DOCUMENTS

| | | |
|---|---|---|
| JP | H06-197901 A | 7/1994 |
| JP | 10-174689 A | 6/1998 |
| JP | 2007-061946 A | 3/2007 |
| JP | 2013-504353 A | 2/2013 |
| JP | 2013-540003 A | 10/2013 |
| WO | 2011/030015 A1 | 3/2011 |
| WO | 2012/040432 A1 | 3/2012 |

OTHER PUBLICATIONS

Sep. 15, 2017 Search Report issued in European Patent Application No. 15748671.3.

* cited by examiner

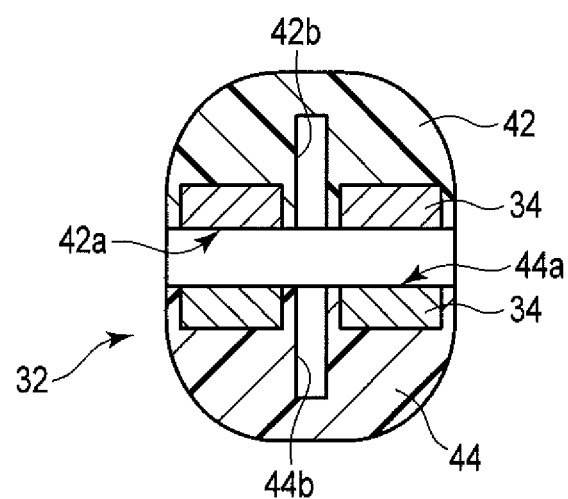
F I G. 1C

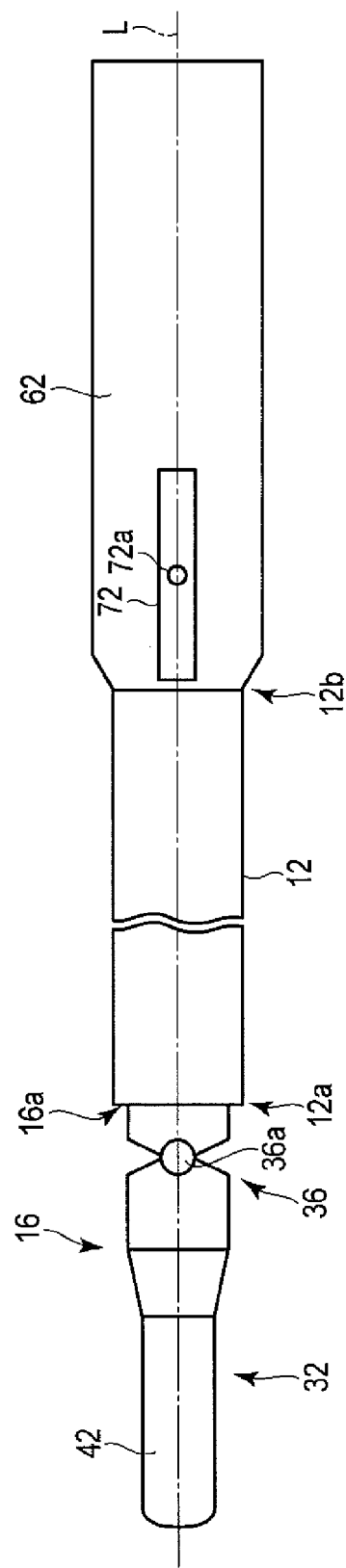
F I G. 2A

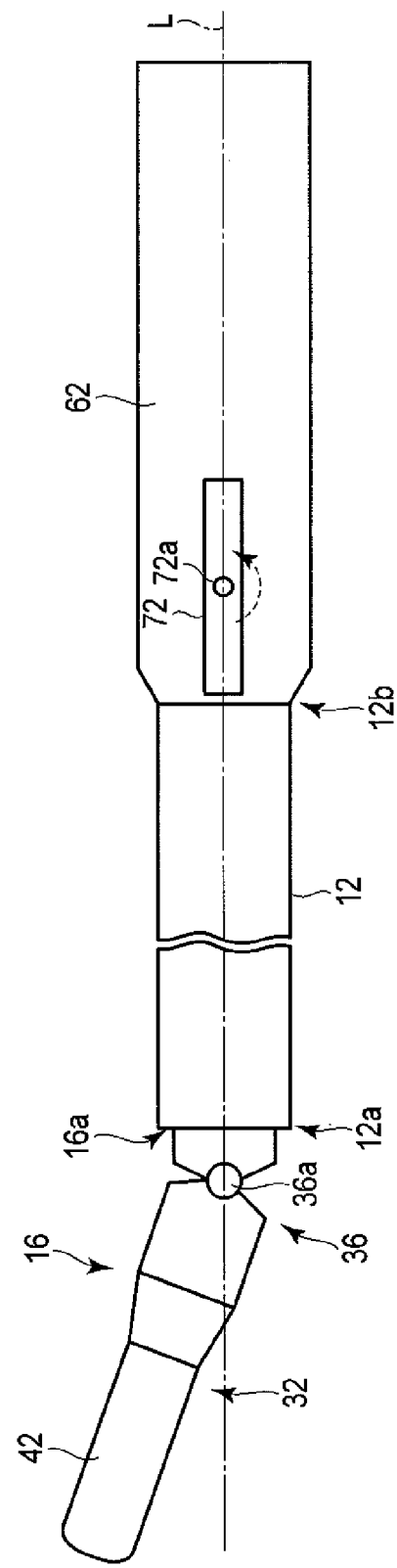
F I G. 2B

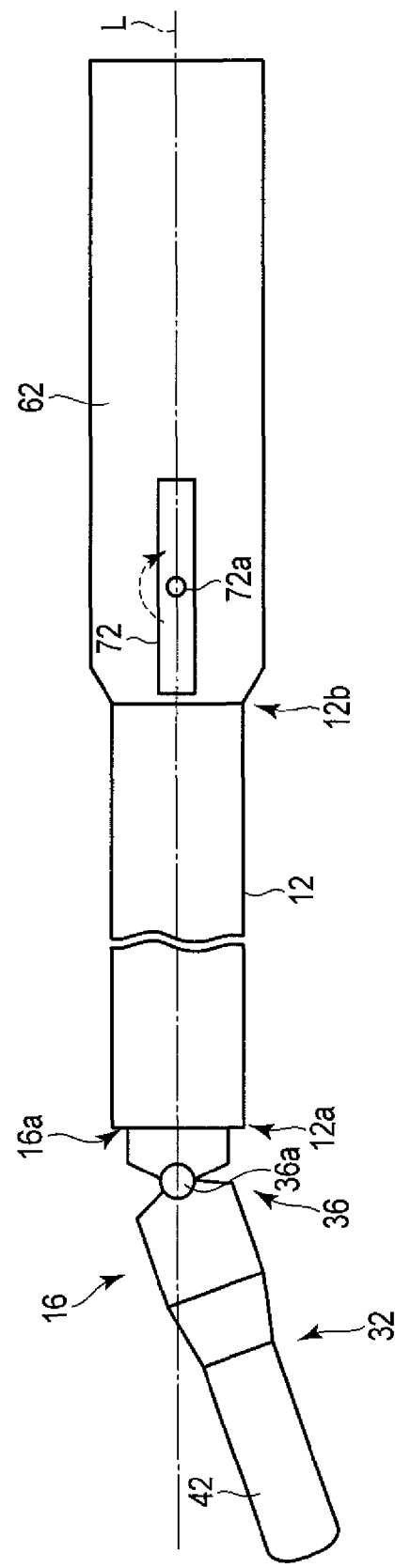
F I G. 2C

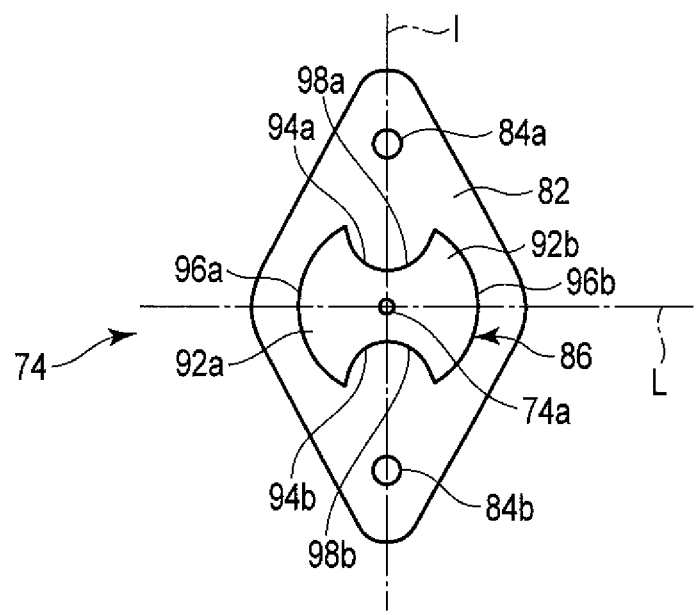
F I G. 3A
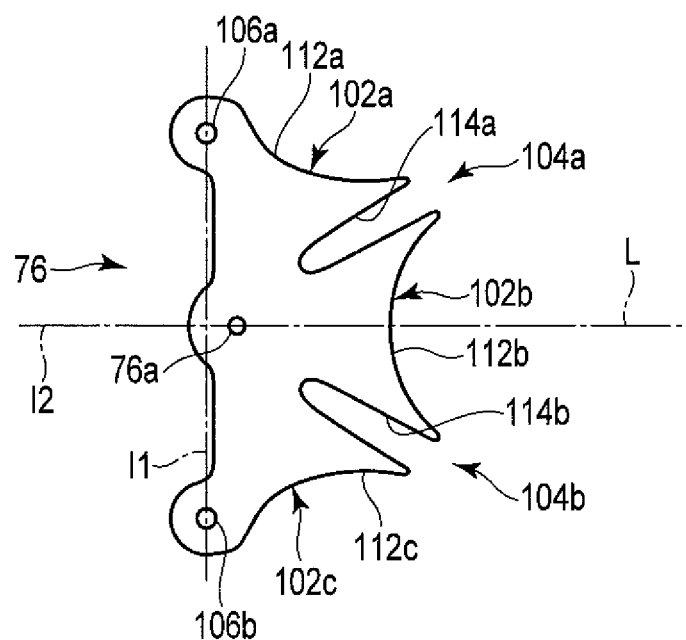
F I G. 3B

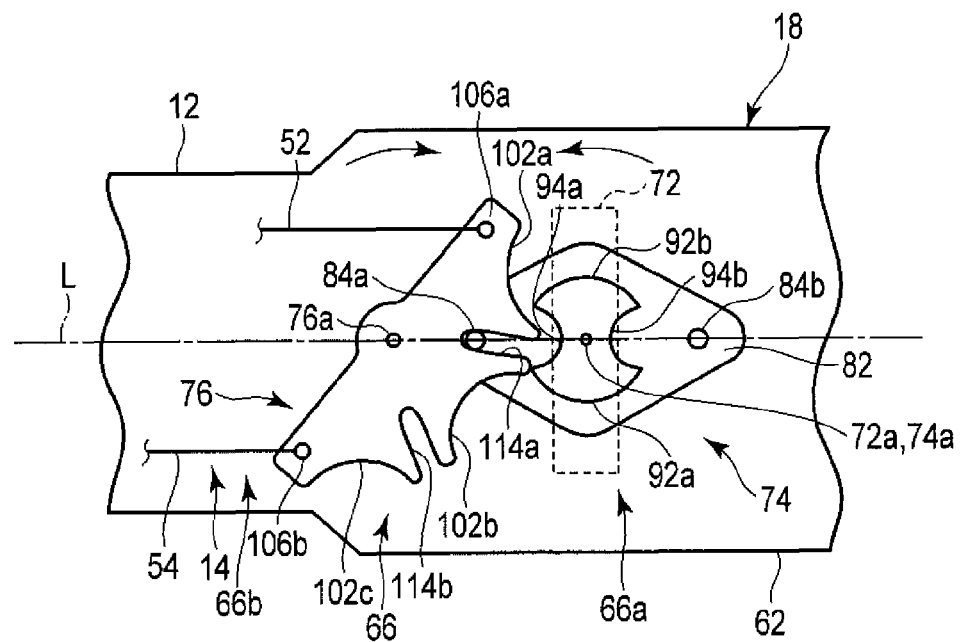
F I G. 4C
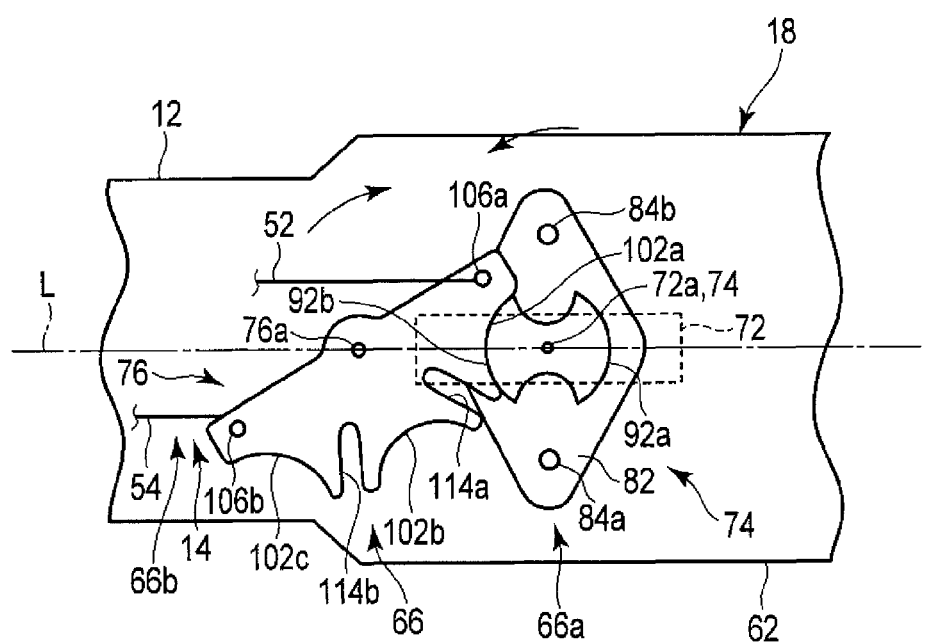
F I G. 4D

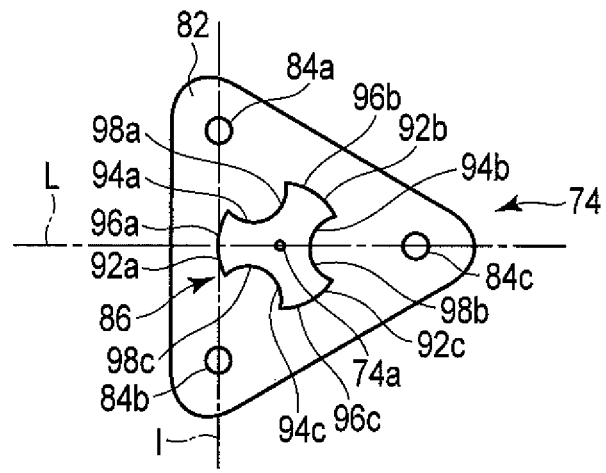
F I G. 7A
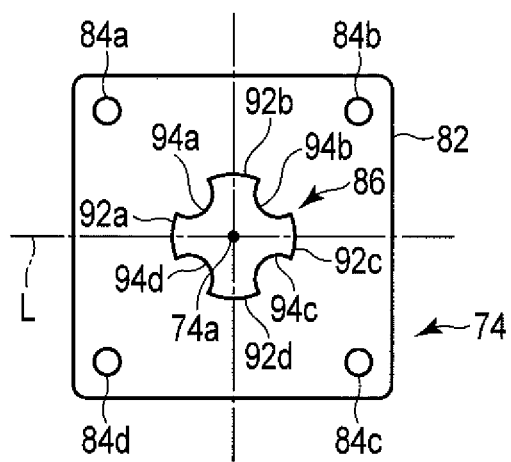
F I G. 7B

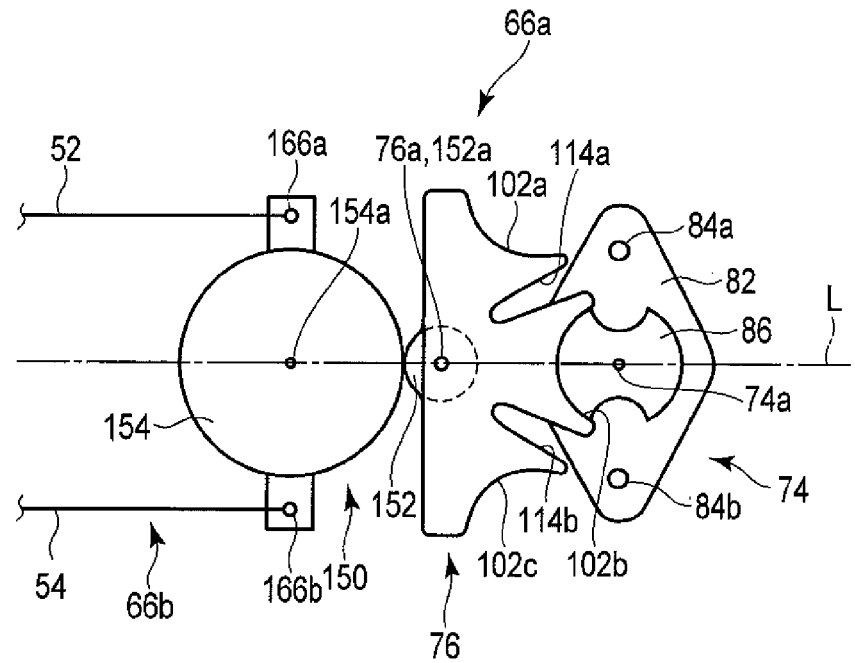
F I G. 8A
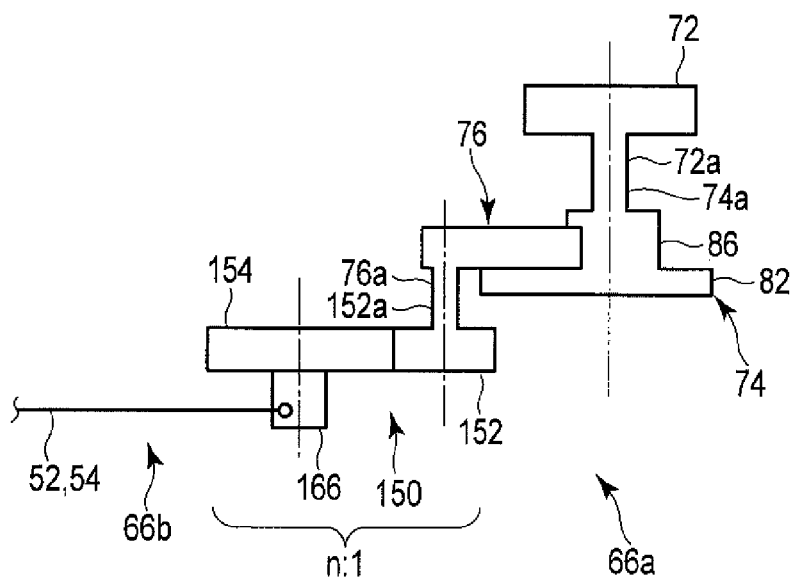
F I G. 8B

TREATMENT DEVICE

CROSS-REFERENCE TO RELATED APPLICATIONS

This application is a Continuation application of PCT Application No. PCT/JP2015/053267, filed Feb. 5, 2015 and based upon and claiming the benefit of priority from prior Japanese Patent Application No. 2014-024754, filed Feb. 12, 2014, the entire contents of all of which are incorporated herein by reference.

BACKGROUND OF THE INVENTION

1. Field of the Invention

The present invention relates to a treatment device which can treat living tissue.

2. Background Art

For example, Jpn. Pat. Appln. KOKAI Publication No. 10-174689 discloses a treatment device which can rotate an end effector relative to a distal end of a sheath by operating an operation section and can maintain a rotated state of the end effecter. The end effector of the treatment device can be opened and closed by operating the operation section. In this treatment device, an operation of opening and closing the end effector and an operation of rotating the end effector relative to the distal end of the sheath are independent of each other. Therefore, when the end effector is opened or closed, the rotated state of the end effector can be maintained.

BRIEF SUMMARY OF THE INVENTION

According to an aspect of the present invention, there is provide a treatment device includes: a sheath including a distal end, a proximal end, and a longitudinal axis defined by the distal end and the proximal end; an end effector that is provided at the distal end of the sheath and that is configured to change its direction relative to the distal end of the sheath; a driving force transmission section that is provided in the sheath to be movable along the longitudinal axis and transmits a driving force to change the direction of the end effector from a proximal end to a distal end; a first rotation portion coupled to the proximal end of the driving force transmission section and configured to rotate around a first rotation shaft to move the driving force transmission section along the longitudinal axis; a second rotation portion that is configured to rotate around a second rotation shaft parallel to and spaced apart from the first rotation shaft, and that switches between a first rotation position, at which the second rotation portion engages with the first rotation portion, transmits rotation motion to the first rotation portion, and transmits the driving force to the driving force transmission section, and the direction of the end effector relative to the distal end of the sheath is changed, and a second rotation position, at which the second rotation portion engages with the first rotation portion, restricts rotation of the first rotation portion, prevents the rotation motion transmitted to the first rotation portion, and prevent movement of the driving force transmission section, and a position of the end effector relative to the distal end of the sheath is maintained; and an operation element that switches the second rotation portion between the first rotation position and the second rotation position.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1C is a schematic transverse sectional view of the holding section of the treatment device according to the first to fifth embodiments, taken along a line 1C-1C in FIG. 1B.

FIG. 2A is a schematic top view of the treatment device according to the first to fifth embodiments, showing that an operation lever disposed in an operation section at a proximal end of a sheath is aligned with a longitudinal axis of the sheath, and the holding section disposed at a distal end of the sheath is aligned with the longitudinal axis of the sheath.

FIG. 2B is a schematic top view of the treatment device according to the first to fifth embodiments, showing that the operation lever disposed in an operation section near a proximal end of the sheath begins to be rotated to deviate its longitudinal direction from the longitudinal axis, specifically, begins to be rotated right from the proximal end to the distal end of the sheath, and the holding section disposed at the distal end of the sheath is rotated right from the distal end of the sheath.

FIG. 2C is a schematic top view of the treatment device according to the first to fifth embodiments, showing that the operation lever disposed in an operation section near a proximal end of a sheath begins to be rotated to deviate its longitudinal direction from the longitudinal axis, specifically, begins to be rotated left from the proximal end to the distal end of the sheath, and the holding section disposed at the distal end of the sheath is rotated left from the distal end of the sheath.

FIG. 3A is a schematic view of an input side rotation portion of a unidirectional driving force transmission mechanism disposed inside the operation section of the treatment device according to the first embodiment.

FIG. 3B is a schematic view of an output side rotation portion of a unidirectional driving force transmission mechanism disposed inside the operation section of the treatment device according to the first embodiment.

FIG. 4C is a schematic view of the unidirectional driving force transmission mechanism disposed inside the operation section of the treatment device according to the first embodiment, showing that a fore end of the operation lever is rotated left and a rear end of the operation lever is rotated right to rotate the input side rotation portion, a pin of the input side rotation portion fits in an engagement groove of the output side rotation portion, and the end effector is rotated while the output side rotation portion is rotating.

FIG. 4D is a schematic view of the unidirectional driving force transmission mechanism disposed inside the operation section of the treatment device according to the first embodiment, showing that the operation lever and the input side rotation portion are disposed to a position rotated 180 degrees from the position shown in FIG. 4A, and the end effector is rotated from the distal end of the sheath.

FIG. 7A is a schematic view of an input side rotation portion of a unidirectional driving force transmission mechanism disposed inside the operation section of the treatment device according to the third embodiment.

FIG. 7B is a schematic view of an input side rotation portion of a unidirectional driving force transmission mechanism disposed inside an operation section of the treatment device according to a modification of the third embodiment.

FIG. 8A is a schematic top view of a unidirectional driving force transmission mechanism disposed inside an operation section of the treatment device according to the fourth embodiment.

FIG. 8B is a schematic side view of the unidirectional driving force transmission mechanism disposed inside the operation section of the treatment device according to the fourth embodiment.

DETAILED DESCRIPTION OF THE INVENTION

Embodiments of the present invention will be described with reference to the drawings.

The first embodiment will be described with reference to FIG. 1A to FIG. 4D.

Figure 1A:
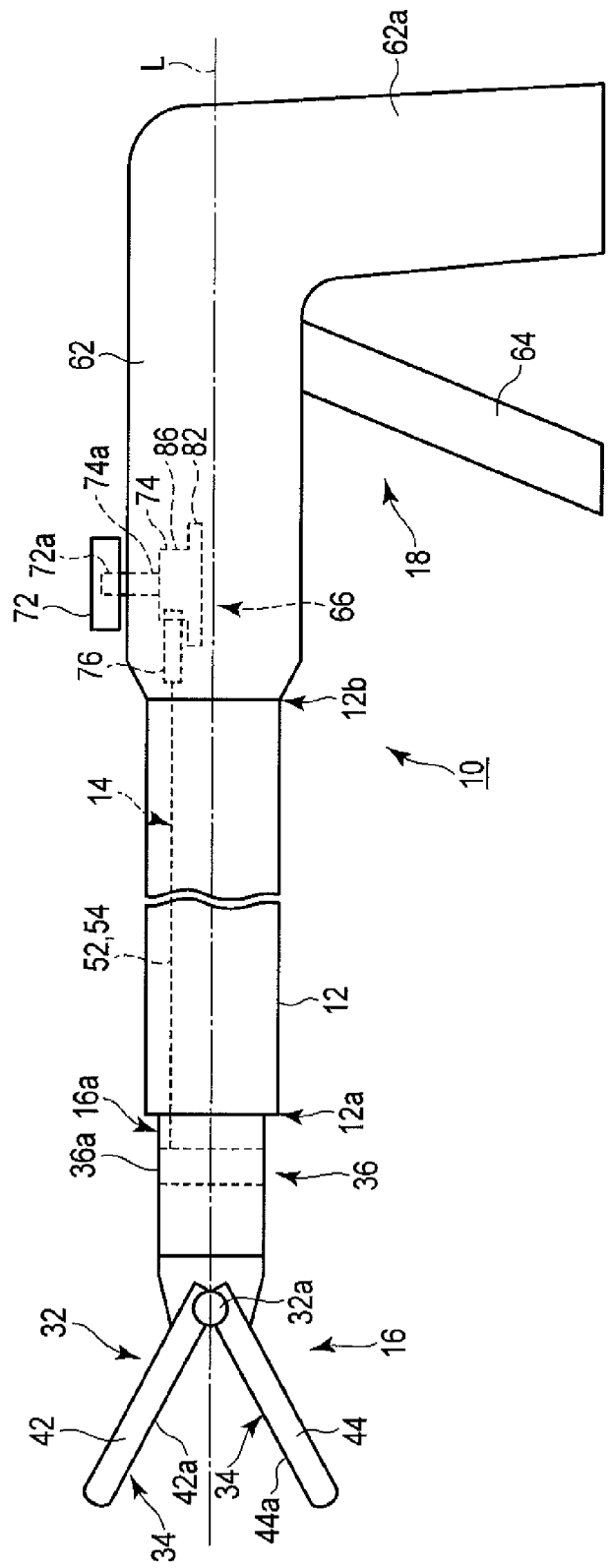
FIG. 1A is a schematic front view of a treatment device according to first to fifth embodiments, showing that a holding section is opened.
Figure 1B:
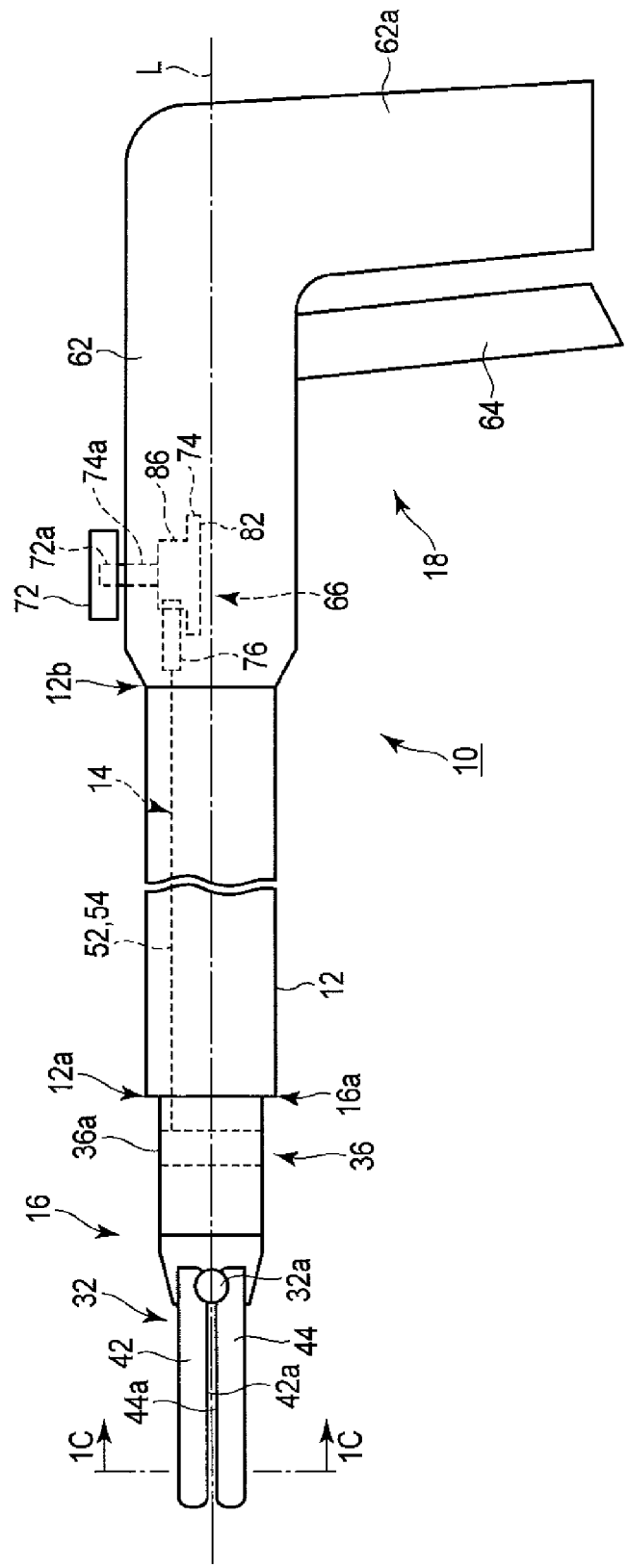
FIG. 1B is a schematic front view of the treatment device according to the first to fifth embodiments, showing that the holding section is closed.

As shown in FIG. 1A and FIG. 1B, a treatment device 10 of this embodiment includes a sheath 12, a driving force transmission section 14, an end effector 16 and an operation section 18.

The sheath 12 is formed of, for example, stainless steel, to be a cylindrical shape. The sheath 12 has a distal end 12a and a proximal end 12b, and a longitudinal axis L is defined by the distal end 12a and the proximal end 12b.

The end effector 16 includes a holding section 32 (see FIG. 1A to FIG. 1C) configured to hold, for example, living tissue, an energy output section 34 (see FIG. 1A and FIG. 1C) which applies energy to the living tissue and treats the living tissue held by the holding section 32, and a rotation section 36 (FIG. 1A, FIG. 1B, and FIG. 2A to FIG. 2C) which opens and closes the holding section 32.

The holding section 32 includes a first holding member 42 including a first holding surface 42a, and a second holding member 44 including a second holding surface 44a. The first and second holding members 42 and 44 are connected to an opening and closing lever 64 (to be described later) of the operation section 18, a driving force is transmitted to the first and second holding members 42 and 44 via an opening and closing drive shaft (not shown) passing through the sheath 12, and the first and second holding members 42 and 44 are opened and closed via a pivotally supporting section 32a. It is preferable that the opening and closing drive shaft be a wire, or a plurality of rod members. The rod members are connected to one another at rotatable positions.

It is preferable that the energy output section 34 be arranged on both or either one of the first holding surface 42a and the second holding surface 44a. The energy output section 34 may be configured as appropriate to output high-frequency energy using a high-frequency electrode, ultrasonic vibration energy by ultrasonic vibrations oscillated from an ultrasonic transducer, heat energy using a heater, etc. It is desirable that the energy output section 34 be substantially U-shaped or the like, so that energy can be continuously applied to living tissue. It is desirable that guide grooves 42a and 42 be formed in inner parts of the energy output section 34 to take in and out a cutter (not shown) which cuts a dehydrated part of living tissue by applying energy. The cutter preferably has flexibility to be bent in accordance with rotation of the end effector.

In this embodiment, as shown in FIG. 1A, FIG. 1B, and FIG. 2A to FIG. 2C, the rotation section 36 rotates the end effector 16 relative to the distal end 12a of the sheath 12 by a shaft member 36a. In other words, the rotation section 36 is formed to change the direction of the end effector 16 relative to the distal end 12a of the sheath 12. Thus, the end effector 16 is provided to be rotatable, or changeable in direction, relative to the distal end 12a of the sheath 12.

The driving force transmission section 14 is provided to be movable along the longitudinal axis L inside the sheath 12. The transmission section 14 includes, for example, a pair of driving shafts 52 and 54 formed of wires or rods. The pair of driving shafts 52 and 54 form a link mechanism 66b having, for example, a substantially parallelogram shape as conventionally known, in cooperation with a proximal end 16a of the end effector 16 and a unidirectional driving force transmission mechanism 66a (to be described later) of the operation section 18. Thus, the driving force transmission section 14 can transmit the driving force from the operation section 18 through its proximal end to distal end to rotate the end effector 16 relative to the distal end 12a of the sheath 12 and change the direction of the end effector 16.

The operation section 18 includes an operation section main body 62 including a grip 62a, the opening and closing lever 64 which relatively opens and closes the first and second holding members 42 and 44 of the end effector 16, and a rotation mechanism 66 which retains the end effector 16 in a desired rotation state relative to the distal end 12a of the sheath 12. The rotation mechanism 66 is desirably formed of a combination of the unidirectional driving force transmission mechanism 66a and the link mechanism 66b of a parallelogram or the like.

A known mechanism may be used as appropriate for the mechanism which relatively opens and closes the first and second holding members 42 and 44 of the end effector 16 by operating the opening and closing lever 64.

The unidirectional driving force transmission mechanism 66a includes an operation lever (driving force input section) 72 as an operation element, which is disposed outside the operation section main body 62 and operated by a user (operator) of the treatment device 10, an input side rotation portion (second rotation portion) 74 which is disposed inside the operation section main body 62 and rotated by input of the driving force from the operation lever 72, and an output side rotation portion (first rotation portion) 76 which is connected to the driving force transmission section 14. The unidirectional driving force transmission mechanism 66a allows unidirectional transmission of the driving force from the input side rotation portion 74 to the output side rotation portion 76, but restricts or regulates transmission of the driving force from the output side rotation portion 76 to the input side rotation portion 74.

The operation lever 72 is desirably disposed around the proximal end 12b of the sheath 12. Assuming that the direction of opening and closing the first and second holding members 42 and 44 is defined as up-down directions, it is preferable that the operation lever 72 be disposed in an upper side of the proximal end 12b of the sheath 12. The operation lever 72 is configured to rotate around a rotation shaft 72a as a fulcrum, and to input the driving force to the input side rotation portion 74. The operation lever 72 has a rod shape, whose longitudinal direction may be parallel to the longitudinal axis L of the sheath 12 depending on its arrangement. The end effector 16 is disposed at the distal end 12a of the sheath 12 to be adjusted to align with the longitudinal axis L, when the longitudinal direction of the operation lever 72 is parallel to the longitudinal axis L of the sheath 12. The operation lever 72 is set to increase a rotation angle of the end effector 16 relative to the distal end 12a of the sheath 12 as the longitudinal direction of the operation lever 72 deviates from the longitudinal axis L.

The input side rotation portion 74 is configured to rotate around an input side rotation shaft (central shaft) 74a perpendicular to the longitudinal axis L of the sheath 12 as a fulcrum. In other words, the input side rotation portion 74 is rotatable around the input side rotation shaft 74a. The input side rotation shaft 74a of the input side rotation portion 74 is coaxial with the rotation shaft 72a of the operation lever 72 in this embodiment. Therefore, the input side rotation portion 74 is rotated in association with the operation lever 72 rotated by the user, and receives the driving force. The input side rotation shaft (second rotation shaft) 74a is parallel to and spaced apart from an output side rotation shaft (first rotation shaft) 76a to be described later.

The operation lever 72 is supported to create moderate friction against the operation section main body 62 to prevent the operation lever 72 and the input side rotation portion 74 from rotating on its own due to gravity or the like, even if the output side rotation portion 76 does not exist. Although not shown in the drawings, it is desirable that, for example, an O ring be disposed between the operation section main body 62 and the rotation shaft 72a. The friction between the operation lever 72 and the operation section main body 62 is of a degree that maintains a relative position therebetween when the user does not touch the operation lever 72, and allows the operation lever 72 to freely rotate relative to the operation section main body 62 when the user is operating the operation lever 72.

As shown in FIG. 3A, the input side rotation portion 74 includes a base 82, a plurality of pins (first engagement portions) 84a and 84b, and an input cam 86 disposed on the base 82. The pins 84a and 84b and the input cam 86 are disposed on one (a front surface) of the two surfaces (the front surface and a rear surface) of the base 82.

The base 82 in this embodiment has an almost rhomboidal shape having two diagonal lines (a major axis and a minor axis). The input side rotation shaft 74a is located at an intersection of the two diagonal lines, that is, the center of gravity of the base 82.

In this embodiment, the pins 84a and 84b are located in positions near the vertexes on the major axis of the two diagonal lines of the rhomboidal base 82. The pins 84a and 84b are on the opposite sides of the input side rotation shaft 74a at the same distance from the input side rotation shaft 74a. Furthermore, the pins 84a and 84b are inserted in and drawn out of engagement grooves (first engagement grooves) 114a and 114b (to be described later) of the output side rotation portion 76 in accordance with axial rotation around the input side rotation shaft 74a. Thus, the driving force can be applied to the output side rotation portion 76 by means of the pins 84a and 84b of the input side rotation portion 74.

The input cam 86 is formed integrally with the base 82. The input cam 86 includes two convex portions (second convex portions) 92a and 92b as engagement portions (second engagement portions), to which normal lines are provided on the opposite sides of the input side rotation shaft 74a, and two concave portions (second concave portions) 94a and 94b on the opposite sides of the input side rotation shaft 74a. The pair of convex portions 92a and 92b are symmetrical to each other with respect to the input side rotation shaft 74a. In other words, the convex portions 92a and 92b of the input side rotation portion 74 comprise convex portions (second engagement grooves) 92a and 92b projecting in radial directions of the rotation shaft 74a. The two concave portions 94a and 94b are symmetrical to each other with respect to the input side rotation shaft 74a.

The two convex portions 92a and 92b respectively comprise arc surfaces 96a and 96b centering on the input side rotation shaft 74a. In this embodiment, the arc surfaces 96a and 96b fall within the range of approximately 90 degrees around the input side rotation shaft 74a as the center. The two concave portions 94a and 94b have edges 98a and 98b closer to the input side rotation shaft 74a than the arc surfaces 96a and 96b. The edges 98a and 98b of the concave portions 94a and 94b may have any shape as long as those edges are concave with respect to the convex portions 92a and 92b, but may preferably be arc-shaped. The edges 98a and 98b may also be shaped in a substantially U shape, for example.

The pins 84a and 84b are farther away from the input side rotation shaft 74a than the arc surfaces 96a and 96b of the convex portions 92a and 92b. The pins 84a and 84 face the edges 98a and 98b of the concave portions 94a and 94b, and are located outside a region radially extending over the arc surfaces 96a and 96b having the center at the input side rotation shaft 74a.

It is preferable that the input side rotation portion 74 be symmetrical with respect to the longitudinal axis L in FIG. 3A and symmetrical with respect to an imaginary line I passing through the pins 84a and 84b and perpendicular to the longitudinal axis L, when the minor axis of the rhomboidal base 82 coincides with the longitudinal axis L.

The output side rotation portion (output cam) 76 is configured to rotate around the output side rotation shaft (second central shaft) 76a parallel to and spaced apart from the input side rotation shaft 74a as a fulcrum. It is preferable that an imaginary line segment connecting the input side rotation shaft 74a and the output side rotation shaft 76a be on the longitudinal axis L.

The output side rotation portion 76 includes an odd number (preferably, three or more) of concave portions (second engagement grooves) 102a, 102b, and 102c, convex portions (first convex portions) 104a and 104b formed adjacently between two of the concave portions (first concave portions) 102a, 102b, and 102c having a fulcrum at the output side rotation shaft 76a, and a pair of coupling portions 106a and 106b to which proximal ends 52a and 54a of the driving shafts 52 and 54 are coupled. The concave portion 102b is formed between the convex portions 104a and 104b. The concave portion 102a is formed between the coupling portion 106a and the convex portion 104a. The concave portion 102c is formed between the coupling portion 106b and the convex portion 104b. Thus, the coupling portions 106a and 106b function as convex portions as well as the convex portions 104a and 104b. The concave portions 92a and 92b of the input side rotation portion 74 are fit in the concave portions 102a, 102b, and 102c. Since the convex portions 104a and 104b are interposed adjacently between two of the concave portions 102a, 102b, and 102c, provision of an even number of the convex portions 104a and 104b is desirable.

Assume that a first imaginary line I1 passes through the pair of coupling portions 106a and 106b, and a second imaginary line I2 perpendicular to the first imaginary line I1 passes through the rotation shaft 76a, as shown in FIG. 3B. In this case, it is desirable that the output side rotation portion (output cam) 76 is symmetrical with respect to the second imaginary line I2. The concave portion 102b, having an arc surface 112b to be described later, is located on the second imaginary line I2.

The concave portions 102a, 102b, and 102c respectively include arc surfaces (arc-shaped groove surfaces) 112a, 112b, and 112c centering on the input side rotation shaft 74a. In other words, the output side rotation portion 76 includes the concave portions (second engagement grooves) 102a, 102b, and 102c concaved in radial directions of the rotation shaft 76a.

The output side rotation portion 76 includes engagement grooves 114a and 114b as cam grooves between the output side rotation shaft 76a and the convex portions 104a and 104b. Specifically, the convex portions 104a and 104b includes the engagement grooves 114a and 114b, through which the pins 84a and 84b serving as cam pins are inserted and drawn out. Inlet ports of the engagement grooves 114a and 114b are formed at distal portions of the convex portions 104a and 104b distant from the output side rotation shaft 76a. It is preferable that the engagement grooves 114a and 114b be straight in radial directions toward the output side rotation shaft 76a.

When the rotation shaft 74a of the input side rotation portion 74, the inlet port of the engagement groove 114a of the output side rotation portion 76 and the innermost part of the groove are located on a straight line, the distance between the rotation shaft 74a of the input side rotation portion 74 and the pin 84a or 84b is longer than the distance between the rotation shaft 74a of the input side rotation portion 74 and innermost part of the engagement grooves 114a or 114b of the output side rotation portion 76.

In this embodiment, the arc surfaces 112a, 112b, and 112c fall within the range of, for example, approximately 50 degrees around the output side rotation shaft 76a as the center in consideration of the convex portions 104a and 104b. The convex portions 104a and 104b fall within the range of approximately 10 degrees around the output side rotation shaft 76a as the center.

The output side rotation portion 76 is coupled to the driving force transmission section 14; specifically, the proximal ends 52a and 54a of the driving shafts 52 and 54 are coupled to the coupling portions 106a and 106b of the output side rotation portion 76. Therefore, when the output side rotation portion 76 axially rotates around the output side rotation shaft 76a, the pair of driving shafts 52 and 54 can move along the longitudinal axis L inside the sheath 12.

When the end effector 16 is arranged in a straight (or nearly straight) line with respect to the distal end 12a of the sheath 12 (see FIG. 2A), the state is referred to as a neutral state.

Referring to FIGS. 2A to 2C and FIGS. 4A to 4D, in this embodiment, when the operation lever 72 is rotated − (minus) 180 degrees in a direction shown in FIG. 2B from the neutral state shown in FIG. 2A, the end effector 16 is maintained in a state rotated, for example, approximately +60 degrees. In this embodiment, the operation lever 72 is rotated − (minus) 180 degrees in one step. The end effector 16 is rotated, for example, approximately +60 degrees with respect to the neutral state in one step. In this embodiment, the maximum rotation angle in a + (plus) direction is, for example, +60 degrees with respect to the neutral state.

When the operation lever 72 is rotated +180 degrees in a direction shown in FIG. 2C from the neutral state shown in FIG. 2A, the end effector 16 is maintained in a state rotated, for example, approximately −60 degrees. In this embodiment, the operation lever 72 is rotated +180 degrees in one step. The end effector 16 is rotated, for example, approximately −60 degrees with respect to the neutral state in one step. In this embodiment, the maximum rotation angle in a − (minus) direction is, for example, −60 degrees with respect to the neutral state.

An operation of the treatment device 10 according to the embodiment will be described with reference to FIG. 4A to FIG. 4D.

For example, when the end effector 16 is to be inserted into a body cavity, the longitudinal axis of the operation lever 72 is aligned along the longitudinal axis L of the sheath 12 to maintain the neutral state in which the end effector 16 is arranged in a straight line with respect to the distal end 12a of the sheath 12.

At this time, the arc surface 96a of the convex portion 92a, which is one of the convex portions 92a and 92b of the input cam 86 of the input side rotation portion 74, faces the arc surface 112b of the central concave portion 102b, which is one of the three concave portions 102a, 102b, and 102c of the output side rotation portion 76. The convex portion 92a fits in the concave portion 102b.

In this state, there is a possibility of external force being applied to the end effector 16, so that the distal end 12a of the sheath 12 may be deviated from the longitudinal axis L. For example, when the user releases the operation lever 72 from a hand, the external force is transmitted from the end effector 16 to the output side rotation portion 76 through the driving shafts 52 and 54 of the link mechanism 66b. Therefore, the output side rotation portion 76 axially rotates around the output side rotation shaft 76a in accordance with the driving force applied to the link mechanism 66b. However, the external force is not transmitted to the input side rotation portion 74. This is because the arc-shaped convex portion 92a of the input side rotation portion 74 and the arc-shaped concave portion 102b of the output side rotation portion 76, which face each other, merely slide relative to each other, since the convex portion 92a and the concave portion 102b are coaxial arcs with respect to the input side rotation axis 74a as the center. In this embodiment, the concave portion 102b of the output side rotation portion 76 falls within the range of approximately 50 degrees around the central shaft 76a of the output side rotation portion 76. Even if the output side rotation portion 76 is rattled by the external force applied to the end effector 16, the rattle will be limited to a range smaller than that angle (approximately ±25 degrees with respect to the longitudinal axis L). Therefore, the end effector 16 acts to maintain the neural state relative to the distal end 12a of the sheath 12. Thus, the position of the end effector 16 relative to the distal end 12a of the sheath 12 can be maintained.

Figure 4A:
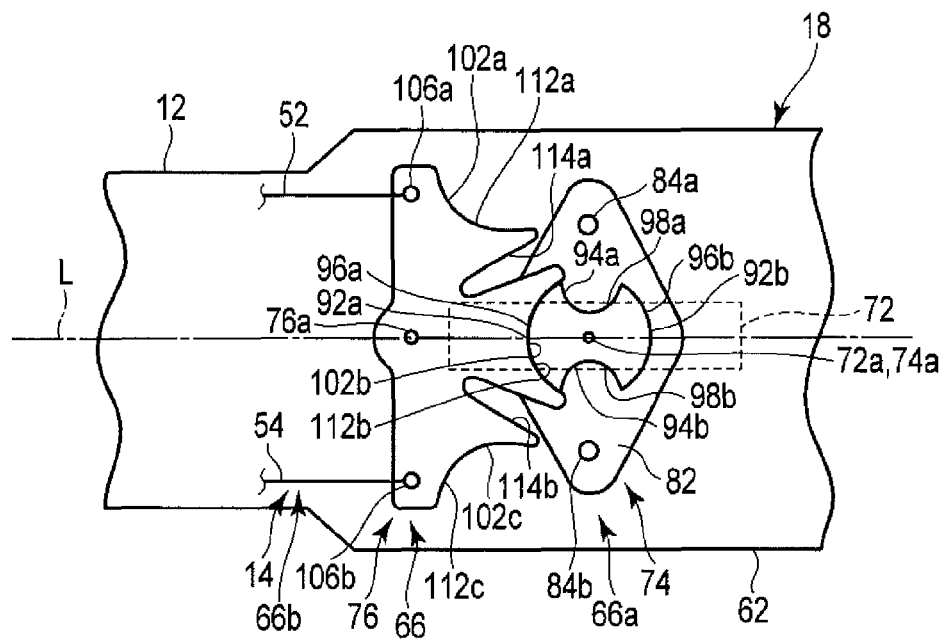
FIG. 4A is a schematic view of the unidirectional driving force transmission mechanism disposed inside the operation section of the treatment device according to the first embodiment, showing that the operation lever is disposed along the longitudinal axis of the sheath, and that the longitudinal axis crosses a first imaginary line passing through the pair of coupling portions at right angles.
Figure 4B:
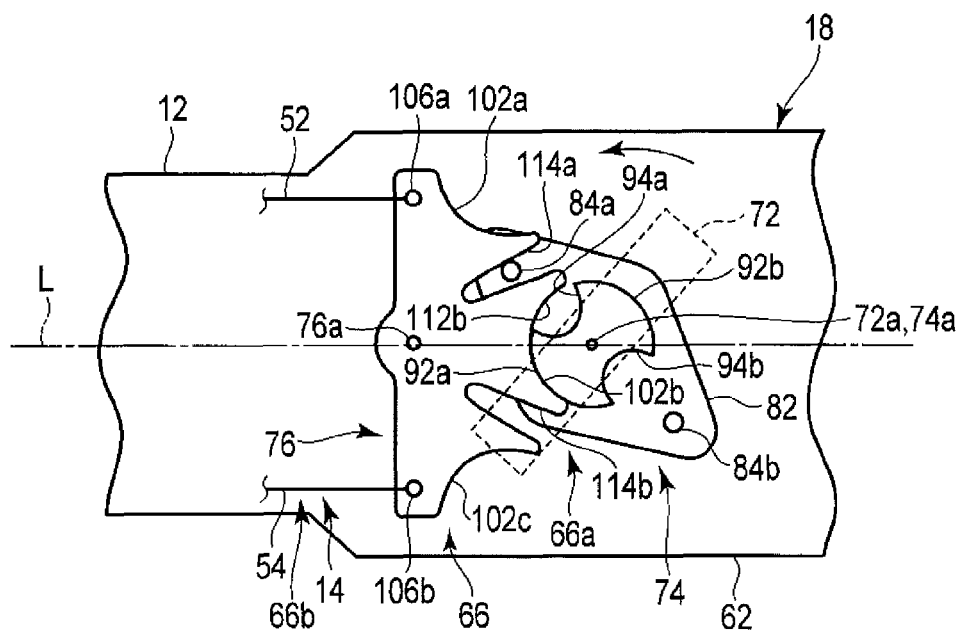
FIG. 4B is a schematic view of the unidirectional driving force transmission mechanism disposed inside the operation section of the treatment device according to the first embodiment, showing that a fore end of the operation lever is rotated left and a rear end of the operation lever is rotated right to rotate the input side rotation portion, and a pin of the input side rotation portion fits in an engagement groove of the output side rotation portion.

In a state where the end effector 16 is located at a desired position in a body cavity or the like, the operation lever 72 begins to be rotated from a state parallel to the longitudinal axis L of the sheath 12 to turn, for example, a front side to the left (downward from the state shown in FIG. 4A to the state shown in FIG. 4B) and a rear side to the right (upward from the state shown in FIG. 4A to the state shown in FIG. 4B). In this embodiment, the operation lever 72 is finally rotated to 180 degrees, as shown in FIG. 2A and FIG. 2B.

As shown in FIG. 4B, the contact state of the convex portion 92a of the input side rotation portion 74 with the concave portion 102b of the output side rotation portion 76 begins to be released. The pin 84a of the input side rotation portion 74 moves from the inlet port of the engagement groove 114a toward the innermost part. Thus, the driving force is transmitted from the input side rotation portion 74 to the output side rotation portion 76, and the output side rotation portion 76 begins to rotate in an opposite direction to that of the input side rotation portion 74. As the output side rotation portion 76 rotates, one driving shaft 52 is pulled toward the proximal end, while the other driving shaft 54 is pushed toward the distal end. Accordingly, the end effector 16 begins to rotate toward the side of the driving shaft 52 at the distal end 12a of the sheath 12.

As shown in FIG. 4C, when the pin 84a of the input side rotation portion 74 reaches the innermost or nearly innermost part of the engagement groove 114a, the contact state (fit state) of the convex portion 92a of the input side rotation portion 74 with the concave portion 102b of the output side rotation portion 76 has been released. Then, the concave portion 94a of the input side rotation portion 74 faces the convex portion 104a of the output side rotation portion 76. At this time, the concave portion 94a of the input side rotation portion 74 moves around the convex portion 104a of the output side rotation portion 76, but is not brought into contact with the convex portion 104a of the output side rotation portion 76.

After the pin 84a of the input side rotation portion 74 reaches the innermost or nearly innermost part of the engagement groove 114a, as the output side rotation portion 76 further rotates, the pin 84a moves in a relative manner toward the inlet port of the engagement groove 114a from the innermost or nearly innermost part. Then, the concave portion 94a of the input side rotation portion 74 moves so as to step over the convex portion 104a of the output side rotation portion 76.

Immediately before the pin 84a is removed from the engagement groove 114a, the convex portion 92b of the input side rotation portion 74 starts to contact the concave portion 102a of the output side rotation portion 76. When the pin 84a is removed from the engagement groove 114a, the convex portion 92b of the input side rotation portion 74 is kept in contact with and fits in the concave portion 102a of the output side rotation portion 76. Therefore, the position of the output side rotation portion 76 relative to the input side rotation portion 74 is maintained, and the end effector 16 is maintained in the state of being rotated in the side of the driving shaft 52, which is pulled to the distal end 12a of the sheath 12.

At this time, as shown in FIG. 4D, the pin 84a is removed from the engagement groove 114a in the state where the output side rotation portion 76 has been rotated from the neutral state (see FIG. 4A). In this embodiment, the pin 84a moves from the position shown in FIG. 4A to the position shown in FIG. 4D. The convex arc surface 96b opposite to the convex arc surface 96a in the input side rotation portion 74 in the neutral state contacts and fits in the concave arc surface 112a, not the central convex arc surface 112b in the output side rotation portion 76 in the neutral state. At this time, as mentioned above, the position of the end effector 16 relative to the distal end 12a of the sheath 12 can be maintained. Accordingly, the output side rotation portion 76 is prevented from rotating on its own relative to the input side rotation portion 74.

Thus, in the state where the condition of the end effector 16 rotated relative to the distal end 12a of the sheath 12 is maintained, the distal end of the end effector 16 is faced to living tissue to be treated in the body cavity. In this state, the living tissue to be treated and the distal end of the end effector 16 are observed via an endoscope or the like (not shown).

The user operates the opening and closing lever 64 of the operation section 18, opens the first and second holding sections 42 and 44 that have been closed, moves the end effector 16 as appropriate to place the living tissue to be treated between the first and second holding sections 42 and 44, and immediately closes the first and second holding sections 42 and 44. Thus, the living tissue to be treated is held between the first and second holding sections 42 and 44. Energy is applied to the living tissue held between the first and second holding sections 42 and 44 to appropriately treat the living tissue.

There is a possibility of external force being applied to the end effector 16, which has been rotated at the distal end 12a of the sheath 12. In this case also, the position of the end effector 16 relative to the distal end 12a of the sheath 12 can be maintained. The end effector 16 is maintained at the rotated state relative to the distal end 12a of the sheath 12. Accordingly, the output side rotation portion 76 is prevented from rotating on its own relative to the input side rotation portion 74. Thus, in the treatment device 10 of this embodiment, when the end effector 16 is rotated a predetermined angle (in this embodiment, a neutral state, +60 degrees, or −60 degrees) relative to the distal end 12a of the sheath 12, the treatment device 10 has rigidity to maintain the end effector 16 at the predetermined rotation angle.

The end effector 16 may be used to perform an operation of pushing living tissue away while the end effector 16 is appropriately rotated. At this time, the rotation section 36 of the end effector 16 can be appropriately rotated via the operation lever 72, the input side rotation portion 74, the output side rotation portion 76, and the transmission section 14.

Therefore, the living tissue can be pushed away while the end effector 16 is rotated by operating the operation lever 72. When the end effector 16 has been rotated a predetermined angle, the end effector 16 can be maintained at the predetermined angle even if the operation lever 72 is released from the hand. Therefore, the user can easily perform an operation in the body cavity or the like.

As described above, the embodiment acts as follows:

The operation lever 72 allows the input side rotation portion 74 to rotate between the position at which the input side rotation portion 74 is axially rotated around the input side rotation shaft 74a, for example, the pin (engagement portion) 84a is inserted into the engagement groove 114a, the output side rotation portion 76 axially rotates around the output side rotation shaft 76a to move the driving force transmission section 14, and the end effector 16 is rotated relative to the distal end 12a of the sheath 12, and the position at which the input side rotation portion 74 is axially rotated around the input side rotation shaft 74a, the pin (engagement section) 84a comes out of the engagement groove 114a, the input side rotation portion 74 suppresses rotation of the output side rotation portion 76 from axially rotating around the output side rotation shaft 76a and suppresses movement of the driving force transmission section 14, the input side rotation portion 74 fit the output side rotation portion 76, and the position of the end effector 16 relative to the distal end 12a of the sheath 12 is maintained.

According to the treatment device 10 of this embodiment, the end effector 16 is rotatable relative to the distal end 12a of the sheath 12, that is, the direction of the end effector 16 relative to the distal end 12a of the sheath 12 can be changed, by rotating the operation lever 72. After the end effector 16 has been rotated to the predetermined position, that is, the direction has been changed, the rotation state of the end effector 16 relative to the distal end 12a of the sheath 12 (the direction of the end effector 16) can be maintained at the predetermined position. In other words, the operation lever 72 (the input side rotation portion 74) of the treatment device 10 can be switched between: a first rotation position, at which the direction of the end effector 16 relative to the distal end of the sheath 12 is changed by engagement with the output side rotation portion 76 to transmit the rotation motion to the output side rotation portion 76 and transmit the driving force to the driving force transmission section 14; and a second rotation position, at which the position of the end effector 16 relative to the distal end of the sheath 12 is maintained by engagement with the output side rotation portion 76 to restrict the rotation motion of the output side rotation portion 76 to prevent the rotation motion being transmitted to the output side rotation portion 76 and prevent movement of the driving force transmission section 14. Thus, the operation lever 72 can switch the rotation position of the input side rotation portion 74 between the first rotation position and the second rotation position.

In the first rotation position, the pins 84a and 84b of the input side rotation portion 74 engage with the engagement grooves 114a and 114b of the output side rotation portion 76. As the input side rotation portion 74 rotates, the pins 84a and 84b push the engagement grooves 114a and 114b, thereby transmitting the driving force to the output side rotation portion 76. The amount of operation force necessary for operating the operation lever 72 is the amount to push the wall surface of the engagement groove 114a of the output side rotation portion 76 by the pin 84a; the required amount of force is relatively small. Therefore, the burden of operating the operation lever 72 imposed on the user can be reduced.

In the second rotation position, the second engagement portion 92a or 92b engages with the second engagement groove 102a, 102b, or 102c, and can slide in a relative manner against the second engagement groove 102a, 102b, or 102c as the input side rotation portion 74 rotates.

Therefore, in the first rotation position, the direction of the end effector 16 relative to the distal end of the sheath 12 can be changed by rotating the input side rotation portion 74 to insert the pin 84a or 84b in the engagement groove 114a or 114b, and axially rotating the output side rotation portion 76 around the output side rotation shaft 76a to move the driving force transmission section 14. In the second rotation position, the position of the end effector 16 relative to the distal end of the sheath 12 can be maintained by rotating the input side rotation portion 74 to let the pin 84a or 84b come out of the engagement groove 114a or 114b, preventing the output side rotation portion 76 from axially rotating around the output side rotation shaft 76a to restrict movement of the driving force transmission section 14, and to engage the output side rotation portion 76 and the input side rotation portion 74.

The unidirectional driving force transmission mechanism 66a in the operation section 18 of the treatment device 10 according to this embodiment can unidirectionally transmit the driving force from the input side rotation portion 74 to the output side rotation portion 76, but restricts transmission of the driving force from the output side rotation portion 76 to the input side rotation portion 74. Therefore, if the end effector 16 is located in a desired position (in which the convex portion 92a or 92b of the input side rotation portion 74 fits in the concave portion 102a, 102b, or 102c of the output side rotation portion 76), the driving force is prevented from being transmitted from the output side rotation portion 76 to the input side rotation portion 74. Thus, the user can concentrate on an operation of maintaining the position of the end effector 16 without operating the operation lever 72.

Specifically, when the operation lever 72 is operated so that one of the convex portions 92a and 92b of the input side rotation portion 74 faces and fits in one of the concave portions 102a, 102b and 102c of the output side rotation portion 76, the end effector 16 is maintained at a predetermined angle relative to the distal end 12a of the sheath 12. When the end effector 16 is maintained at the predetermined angle relative to the distal end 12a of the sheath 12, the end effector 16 of this embodiment can maintain the predetermined angle relative to the distal end 12a of the sheath 12, although external force is applied to the end effector 16 from living tissue.

Therefore, the end effector 16 can be rotated only when the user positively operates the rotation mechanism 66 to rotate the operation lever 72; that is, the end effector 16 can be prevented from being passively rotated in excess of an appropriate angle when the rotation mechanism 66 is not operated. Thus, even when external force is applied to the end effector 16, transmission of driving force from the output side rotation portion 76 to the input side rotation portion 74 is restricted. Accordingly, the input side rotation portion 74 or the operation lever 72 is prevented from rotating on its own and external forces influencing the end effector 16 can be avoided. The end effector 16 itself has rigidity to maintain the predetermined rotation angle by suppressing an influence of external force on the input side rotation portion 74 and the operation lever 72.

The output side rotation portion 76 includes, between adjacent engagement grooves of the engagement grooves 114a and 114b, the concave portions 102a, 102b, and 102c that are faced to the input side rotation portion 74 by axial rotation of the output side rotation shaft 76a. The input side rotation portion 74 includes the convex portions 92a and 92b that can be engaged by axial rotation of the input side rotation shaft 74a with the concave portion, which is one of the concave portions 102a, 102b, and 102c of the output side rotation portion 76 and which faces the input side rotation portion 74. The input side rotation portion 74 includes the input side concave portions 94a and 94b that are provided between adjacent convex portions of the input side concave portions 92a and 92b and between the input side rotation shaft 74a and the pins 84a and 84b, and that prevent interference with a part between adjacent convex portions of the output side convex portions 104a and 104b of the output side rotation portion 76.

Thus, when the pin 84a is in the engagement groove 114a, the concave portion 94a of the input side rotation portion 74 is located astride the convex portion 104a including the engagement groove 114a of the output side rotation portion 76. To transmit the driving force from the input side rotation portion 74 to the output side rotation portion 76, only the friction between the pin 84a and the engagement groove 114a need be taken into consideration. Therefore, the amount of operation force to rotate the end effector 16 with the operation lever 62 by the user can be kept as small as possible.

Specifically, when the driving force is input to the operation lever 72 to transmit the driving force (rotation force) from the input side rotation portion 74 to the output side rotation portion 76, the pin 84a of the input side rotation portion 74 merely pushes the wall surface of the engagement groove 114a of the output side rotation portion 76. When the input side rotation portion 74 and the output side rotation portion 76 have been rotated to predetermined positions, even if the operation lever 72 is released from the hand, the operation lever 72 and the input side rotation portion 74 are prevented from rotating. At this time, the operation lever 72 need not be held to maintain the positions of the driving shafts 52 and 54. Therefore, according to the treatment device 10 of this embodiment, the operation lever 72 can be rotated with a relatively small amount of operating force.

The unidirectional driving force transmission mechanism 66a allows the driving force input by the operation lever (driving force input section) 72 to be transmitted from the input side rotation portion 74 to the output side rotation portion 76 to rotate the end effector 16 via the transmission section 14. Thus, the direction of the end effector 16 relative to the sheath 12 can be changed and the position of the end effector 16 relative to the sheath 12 can be maintained. On the other hand, transmission of driving force from the output side rotation portion 76 to the input side rotation portion 74 and the operation lever 72 via the end effector 16 and the transmission section 14 is prevented, so that the position of the end effector 16 relative to the sheath 12 can be maintained.

The operation lever 72 allows the input side rotation portion 74 to rotate between the position at which the input side rotation portion 74 is rotated to insert the pin 84a into the engagement groove 114a to axially rotate the output side rotation portion 76 around the output side rotation shaft 76a and move the transmission section 14 and at which the end effector 16 is rotated relative to the distal end 12a of the sheath 12, and the position at which the input side rotation portion 74 is rotated to let the pin 84a out of the engagement groove 114a to prevent the output side rotation portion 76 from axially rotating around the output side rotation shaft 76a and suppressing movement of the transmission section 14, and at which the output side rotation portion 76 and the input side rotation portion 74 contact each other to maintain the position of the end effector 16 relative to the distal end 12a of the sheath 12.

In this embodiment, a Geneva drive is used as the unidirectional driving force transmission mechanism 66a; however, a variety of mechanisms may be used if they are formed to transmit the driving force from the input side rotation portion 74 to the output side rotation portion 76 and cannot transmit the driving force from the output side rotation portion 76 to the input side rotation portion 74.

Figure 5:
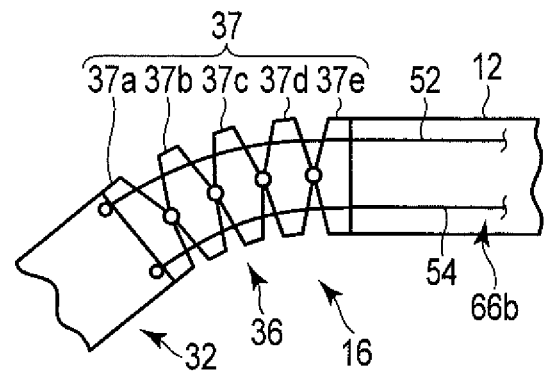
FIG. 5 is a schematic view showing a modification of a rotation section of the treatment device according to the first to fifth embodiments.

In this embodiment, the rotation section 36 is formed to rotate and change the direction of the end effector 16 relative to the distal end 12a of the sheath 12 by, for example, the single shaft member 36a. However, as shown in FIG. 5, the rotation section 36 may be formed as a bending tube 37 including a plurality of bending pieces 37a, 37b, 37c, 37d, and 37e, which is generally used in a bent portion of an endoscope or the like. The bending tube 37 can change the direction of the end effector 16 relative to the distal end 12a of the sheath 12.

Also in the case of using the curved tube 37 as the rotation section 36, the end effector 16 is rotatable relative to the distal end 12a of the sheath 12, that is, the direction of the end effector 16 can be changed, by rotating the operation lever 72. After the end effector 16 has been rotated to the predetermined position, that is, the direction has been changed, the rotation state of the end effector 16 relative to the distal end 12a of the sheath 12 (the direction of the end effector 16) can be maintained at the predetermined position.

The second embodiment is explained below with reference to FIG. 6. The embodiment is a modification of the first embodiment. The same members or the members having the same functions as those of the members of the first embodiment are identified by the same reference symbols as those used for the first embodiment as much as possible, and detailed explanations thereof are omitted.

Figure 6:
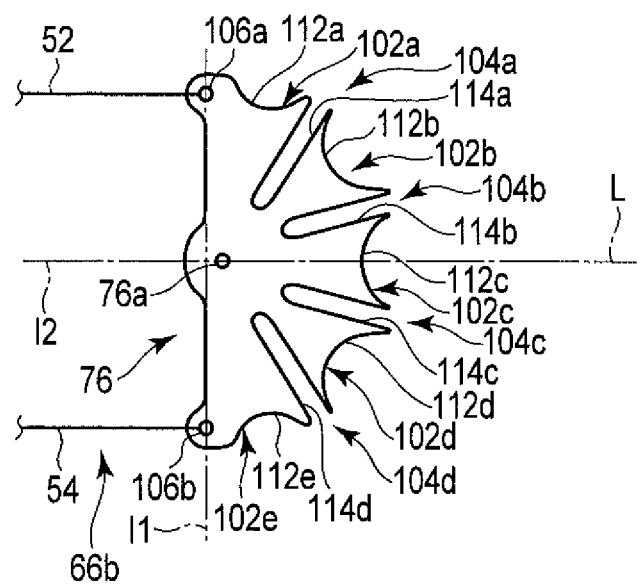
FIG. 6 is a schematic view of an output side rotation portion of a unidirectional driving force transmission mechanism disposed inside an operation section of the treatment device according to the second embodiment.

As shown in FIG. 6, an output side rotation portion 76 of this embodiment differs in shape from the output side rotation portion 76 shown in FIG. 3B.

The output side rotation portion 76 of this embodiment includes five (three or more odd numbers) concave portions 102a, 102b, 102c, 102d, and 102e, and four convex portions 104a, 104b, 104c, and 104d. The concave portion 102b is formed between the convex portions 104a and 104b, the concave portion 102c is formed between the convex portions 104b and 104c, and the concave portion 102d is formed between the convex portions 104c and 104d. The concave portion 102a is formed between a coupling portion 106a and the convex portion 104a. The concave portion 102d is formed between a coupling portion 106b and the convex portion 104d. Thus, the coupling portions 106a and 106b function as convex portions as well as the convex portions 104a, 104b, 104c and 104d.

The concave portions 102a, 102b, 102c, 102d, and 102e respectively include arc surfaces 112a, 112b, 112c, 112d, and 112e centering on the input side rotation shaft 74a. The arc surfaces 112a, 112b, 112c, 112d, and 112e each fall within the range of approximately 30 degrees around the input side rotation shaft 74a as the center. The concave portion 102c having the arc surface 112c is located on a second imaginary line 12.

The convex portions 104a, 104b, 104c, and 104d include a plurality of engagement grooves 114a, 114b, 114c, and 114d, through which a pin 84a or 84b of an input side rotation portion 74 (see FIG. 3A) is inserted and drawn out. It is preferable that the engagement grooves 114a, 114b, 114c, and 114d be straight in radial directions toward the output side rotation shaft 76a.

In this embodiment, a rotation angle of the output side rotation portion 76 relative to the neutral state is greater than that of the output side rotation portion 76 of the first embodiment. Therefore, the end effector 16 of this embodiment rotates, for example, ±72 degrees at maximum.

In this embodiment, the end effector 16 rotates from the neutral state to the maximum 72 degree angle through two steps: it rotates approximately 36 degrees through one step, and approximately 36 degrees through the other step. When an operation lever 72 is rotated 180 degrees from the neutral state shown in FIG. 2A, the amount of rotation (rotation angle) relative to the output side rotation shaft 76a is smaller than that in the first embodiment. At this time, the end effector 16 is maintained in a state rotated approximately 36 degrees relative to the neutral state. When the operation lever 72 is further rotated 180 degrees, the output side rotation shaft 76a is further rotated. At this time, the end effector 16 is maintained in a state rotated approximately 72 degrees relative to the neutral state.

Using the output side rotation portion 76 of this embodiment, the end effector 16 can be maintained at a greater number of positions at angles (predetermined angles) relative to the sheath 12 than the first embodiment. Accordingly, the user can more precisely set rotation angles of the end effector 16 relative to the distal end 12a of the sheath 12, and increase the efficiency of treatment of living tissue.

In this embodiment, the output side rotation portion 76 includes the five (three or more odd numbers) concave portions 102a, 102b, 102c, 102d, and 102e, and the four convex portions 104a, 104b, 104c, and 104d. The output side rotation portion 76 may also be formed to include seven or nine (odd numbered) concave portions, although not shown in the drawings. If the number of concave portions of the output side rotation portion 76 increases, instead of an odd number of concave portions, an even number of concave portions is also acceptable.

The input side rotation portion 74 used in this embodiment is the same as that of the first embodiment described above; however, an input side rotation portion 74 in a third embodiment including a modification is also applicable.

The third embodiment will be described with reference to FIG. 7A. This embodiment is a modification of the first and second embodiments. The same members or the members having the same functions as those of the members of the first and second embodiments are identified by the same reference symbols as those used for those embodiments as much as possible, and detailed explanations thereof are omitted.

As shown in FIG. 7A, an input side rotation portion 74 of this embodiment differs in shape from the input side rotation portion 74 shown in FIG. 3A of the first embodiment described above.

The input side rotation portion 74 includes a base 82, a plurality of pins 84a, 84b, and 84c, and an input cam 86 disposed on the base 82.

The base 82 in this embodiment has an almost regular triangle shape. The input side rotation shaft 74a is located at the center of gravity of the base 82.

In this embodiment, the pins 84a, 84b, and 84c are located in positions near the vertexes on the regular triangle base 82. The pins 84a, 84b, and 84c are spaced apart from one another approximately 120 degrees around the input side rotation shaft 74a at the same distance from the input side rotation shaft 74a. Furthermore, the pins 84a, 84b, and 84c are inserted in and drawn out of engagement grooves 114a, 114b, 114c, and 114d (to be described later) of the output side rotation portion 76 in accordance with axial rotation around the input side rotation shaft 74a.

An input cam 86 of the input side rotation portion 74 of this embodiment includes: three convex portions 92a, 92b, and 92c, to which normal lines are provided radially outward from the input side rotation shaft 74a and spaced at approximately 120 degrees from one another; and three concave portions 94a, 94b, and 94c, to which normal lines are provided radially outward from the input side rotation shaft 74a spaced at approximately 120 degrees from one another.

In the input side rotation portion 74 of this embodiment, the pins 84a, 84b, and 84c are located at approximately 120 degrees with one another around the input side central shaft 74a. The convex portions 92a, 92b, and 92c are formed to be adjacently located between two of the pins 84a, 84b, and 84c. In other words, the pins 84a, 84b, and 84c are located in positions facing the concave portions 94a, 94b, and 94c.

The three convex portions 92a, 92b, and 92c respectively include arc surfaces 96a, 96b, and 96c centering on the input side rotation shaft 74a. In this embodiment, the arc surfaces 96a, 96b, and 96c fall within the range of approximately 60 degrees around the input side rotation shaft 74a as the center. The three concave portions 94a, 94b, and 94c have edges 98a, 98b, and 98c closer to the input side rotation shaft 74a than the arc surfaces 96a, 96b, and 96c. The edges 98a, 98b, and 98c of the concave portions 94a, 94b, and 94c may have any shape as long as the edges are concave with respect to the convex portions 92a, 92b, and 92c.

The pins 84a, 84b, and 84c are farther away from the input side rotation shaft 74a than the arc surfaces 96a, 96b, and 96c of the convex portions 92a, 92b, and 92c. The pins 84a, 84b, and 84c face the edges 98a, 98b, and 98c of the concave portions 94a, 94b, and 94c, and are located outside a region radially extending over the arc surfaces 96a, 96b, and 96c centering on the input side rotation shaft 74a.

It is preferable that the input side rotation portion 74 be symmetrical with respect to the longitudinal axis L in FIG. 7A, when a line passing through and perpendicular to an imaginary line segment I connecting the pins 84a and 84b of the base 82 at the middle point of the line segment I coincides with the longitudinal axis L.

In this embodiment, the output side rotation portion 76 can be rotated approximately 60 degrees as shown in FIG. 4A and FIG. 4D by rotating the input side rotation portion 74 at a smaller angle (approximately 120 degrees) than the angle that the input side rotation portion 74 of the first embodiment rotates.

Although not shown in the drawings, in a case of using the output side rotation portion 76 of the second embodiment, the output side rotation portion 76 can be rotated approximately 36 degrees when the input side rotation portion 74 of this embodiment is rotated 120 degrees.

The input side rotation member 74 may have a structure, as shown in FIG. 7B, in which a base 82 is rectangular, for example, almost square, and pins 84a, 84b, 84c, and 84d are formed near the corners. In this case, an input cam 86 includes four convex portions 92a, 92b, 92c, and 92d, and four concave portions 94a, 94b, 94c, and 94d. The pins 84a, 84b, 84c, and 84d face the concave portions 94a, 94b, 94c, and 94d. The input side rotation member 74 thus formed can also be used as well as the input side rotation member 74 of the first and third embodiments. The output side rotation portion 76 can be rotated approximately 60 degrees as shown in FIG. 4A and FIG. 4D by rotating the input side rotation member 74 shown in FIG. 7B at a smaller angle (approximately 90 degrees) than the angle that the input side rotation portion 74 of the first embodiment rotates.

In a case of using the output side rotation portion 76 of the second embodiment, the output side rotation portion 76 of the second embodiment can be rotated approximately 36 degrees when the input side rotation portion 74 of the third embodiment is rotated 90 degrees.

A fourth embodiment will be described with reference to FIG. 8A and FIG. 8B. This embodiment is a modification of the first to third embodiments. The same members or the members having the same functions as those of the members of the first to third embodiments are identified by the same reference symbols as those used for those embodiments as much as possible, and detailed explanations thereof are omitted.

As shown in FIG. 8A and FIG. 8B, an operation section 18 includes a gear mechanism 150. The gear mechanism 150 includes a first gear (a small gear in this embodiment) 152 coupled to an output side rotation portion 76 and a second gear (a large gear in this embodiment) 154 disposed between a pair of driving shafts 52 and 54.

The small gear 152 has a rotation shaft (central shaft) 152a in common with a rotation shaft 76a of an output side rotation portion 76. A rotation shaft (central shaft) 154a of the large gear 154 is supported by, for example, an operation section main body 62.

The large gear 154 includes a pair of coupling portions 166a and 166b, which are integral with the large gear 154 and rotate in accordance with axial rotation around the rotation shaft 154a. The pair of coupling portions 166a and 166b are connected to the distal ends of the driving shafts 52 and 54. Thus, in this embodiment, the output side rotation portion 76 does not include a pair of coupling portions 106a and 106b.

The small gear 152 and the large gear 154 mesh with each other. For example, it is assumed that the ratio between the numbers of teeth of the small gear 152 and the large gear 154 is 1:n. In this case, when an operation lever 72 is operated to axially rotate the output side rotation portion 76 around the output side rotation shaft 76a via an input side rotation portion 74, the rotation angle of an end effector 16 relative to the rotation angle of the output side rotation portion 76 can be 1/n. Therefore, the smaller step angle (approximately 60 degrees in FIG. 8A) can be reduced (1/n) by the gear mechanism 150. In other words, the rotation angle (flexion angle) of the end effector 16 can be adjusted at a smaller step angle. Thus, the gear mechanism 150 can adjust the amount of movement of the driving force transmission section 14 along the longitudinal axis L with respect to the amount of rotation of the output side rotation portion 76.

In this embodiment, as described above, the first gear 152 is the small gear and the second gear 154 is the large gear that is larger in diameter than the first gear 152. However, the magnitude relationship therebetween may be reversed.

A fifth embodiment will be described with reference to FIG. 9A and FIG. 9B. This embodiment is a modification of the first to fourth embodiments. The same members or the members having the same functions as those of the members of the first to fourth embodiments are identified by the same reference symbols as those used for those embodiments as much as possible, and detailed explanations thereof are omitted.

Figure 9A:
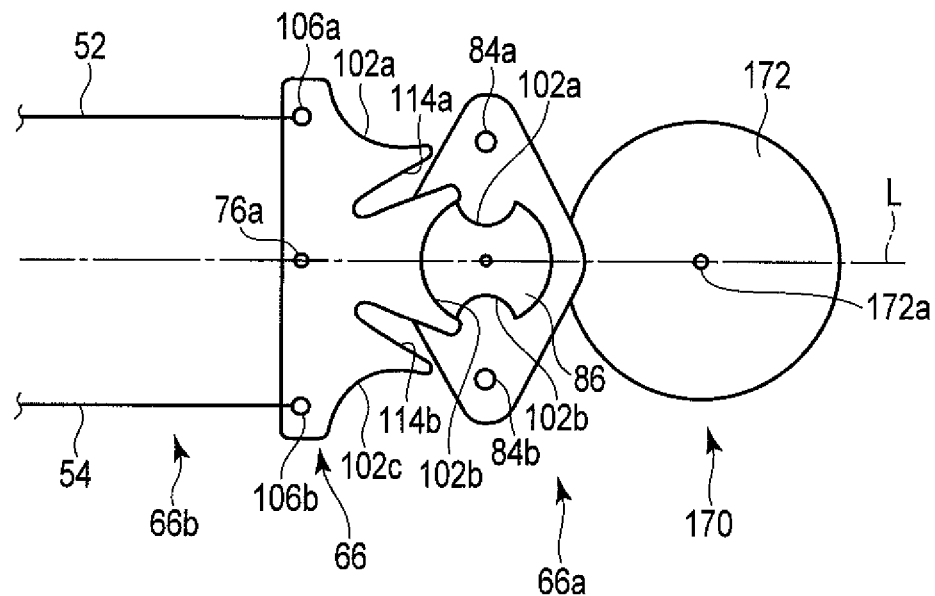
FIG. 9A is a schematic top view of a unidirectional driving force transmission mechanism disposed inside an operation section of the treatment device according to the fifth embodiment.
Figure 9B:
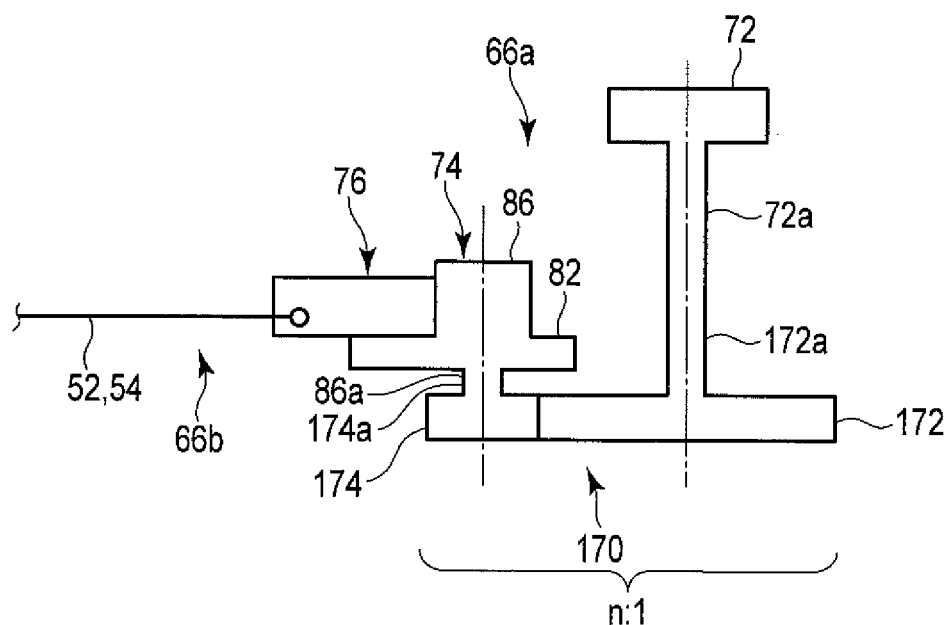
FIG. 9B is a schematic side view of the unidirectional driving force transmission mechanism disposed inside the operation section of the treatment device according to the fifth embodiment.

As shown in FIG. 9A and FIG. 9B, an operation section 18 includes a gear mechanism 170. The gear mechanism 170 of this embodiment differs from the gear mechanism 150 of the fourth embodiment. The gear mechanism 170 includes a first gear (a large gear in this embodiment) 172 integral with an operation lever 72 and a second gear (a small gear in this embodiment) 174 disposed in an input side rotation portion 74.

The large gear 172 has a rotation shaft (central shaft) 172a in common with a rotation shaft 72a of the operation lever 72. The small gear 174 has a rotation shaft (central shaft) 174a in common with a rotation shaft 74a of the input side rotation portion 74.

The large gear 172 and the small gear 174 mesh with each other. For example, it is assumed that the ratio between the numbers of teeth of the large gear 172 and the small gear 174 is 1:n. In this case, when an operation lever 72 is operated to axially rotate the input side rotation portion 74 around the input side rotation shaft 74a, the rotation angle (for example, 180 degrees in this embodiment, as shown in FIG. 9A) of the input side rotation portion 74 relative to the rotation angle of the input side rotation portion 74 can be reduced to 1/n. Therefore, the operation angle (approximately 180 degrees in FIG. 9A) can be reduced (1/n) by the gear mechanism 170. In other words, the rotation angle (flexion angle) of the end effector 16 can be adjusted at a smaller operation angle.

In the first to fifth embodiments described above, the end effector 16 is rotated in an opposite direction to a direction of rotation at a position near the end effector 16 in the operation lever 72. However, the end effector 16 may be rotated in the same direction by, for example, a gear mechanism.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A treatment device comprising:
   a sheath including a distal end, a proximal end, and a longitudinal axis defined by the distal end and the proximal end;
   an end effector that is provided at the distal end of the sheath and that is configured to change direction relative to the distal end of the sheath;
   a driving shaft provided in the sheath that comprises wires that are configured to move only along the longitudinal axis and transmits a driving force to change the direction of the end effector from a proximal end;
   a first rotor coupled to the driving shaft by coupling portions and configured to rotate around a first rotation shaft and extend in a direction intersecting with the longitudinal axis to move the driving shaft along the longitudinal axis;
   a second rotor that is configured to: (1) rotate around a second rotation shaft configured to extend in the direction intersecting with the longitudinal axis and spaced apart from the first rotation shaft, and (2) switch between: (a) a first rotation position, at which the second rotor is configured to engage with the first rotor and transmit rotation motion to the first rotor, and transmit the driving force to the driving shaft, to change the direction of the end effector relative to the distal end of the sheath, and (b) a second rotation position, at which the second rotor is configured to engage with the first rotor to restrict rotation of the first rotor, prevent the rotation motion transmitted to the first rotor, and prevent movement of the driving shaft, to maintain a position of the end effector relative to the distal end of the sheath; and an operation handle configured to switch the second rotor from the first rotation position to the second rotation position.

2. The treatment device according to claim 1, wherein:
the first rotor includes a first engagement groove;
the second rotor includes a first engagement portion configured to fit in the first engagement groove;
the first engagement portion fits in the first engagement groove in the first rotation position, and as the first engagement portion pushes the first engagement groove in accordance with rotation of the second rotor, the driving force is transmitted to the first rotor.

3. The treatment device according to claim 2, wherein:
the first rotor includes a second engagement groove that is concave in a radial direction of the first shaft;
the second rotor includes a second engagement portion that protrudes in a radial direction of the second rotation shaft; and
the second engagement portion fits in the second engagement groove in the second rotation position, and slides relative to the second engagement groove in accordance with rotation of the second rotor.

4. The treatment device according to claim 3, wherein:
the second engagement portion includes an arc surface centering on the second rotation shaft; and
the second engagement groove includes an arc-shaped groove surface centering on the second rotation shaft.

5. The treatment device according to claim 1, wherein:
the first rotor includes a plurality of engagement grooves;
the second rotor includes a plurality of pins that are inserted in and drawn out of the engagement grooves in accordance with axial rotation around the second rotation shaft;
in the first rotation position, the second rotor rotates, the pin is inserted in the engagement groove of the first rotor, the first rotor rotates around the first shaft and moves the driving shaft, and the direction of the end effector relative to the distal end of the sheath is changed; and
in the second rotation position, the second rotor rotates, the pin comes out of the engagement groove of the first rotor, the first rotor suppresses from rotating around the first rotation shaft and suppresses movement of the driving shaft, the second rotor engages with the first rotor, and the position of the end effector relative to the distal end of the sheath is maintained.

6. The treatment device according to claim 1, wherein:
the first rotor includes a plurality of first convex portions, each including an engagement groove, and includes a plurality of first concave portions provided between adjacent first convex portions of the plurality of first convex portions and faced to the second rotor by axial rotation around the first rotation shaft; and
the second rotor includes a plurality of second convex portions configured to fit in the concave portion of the plurality of first concave portions that is faced to the second rotor by axial rotation around the second rotation shaft.

7. The treatment device according to claim 6, wherein:
the second rotor includes a first engagement portion and a second concave portion that is provided between adjacent second convex portions of the plurality of second convex portions and between the first engagement portion and the second rotation shaft, and prevents interference between adjacent convex portions of the plurality of first convex portions of the first rotor.

8. The treatment device according to claim 6, wherein:
the second convex portions of the second rotor include convex arc surfaces centering on the second rotation shaft; and
the first concave portions of the first rotor include concave arc surfaces which the convex arc surfaces fit in.

9. The treatment device according to claim 8, wherein:
the first engagement portion is farther away from the second rotation shaft than the convex arc surfaces, and is located outside a region radially extending over the convex arc surfaces centering on the second rotation shaft.

10. The treatment device according to claim 6, wherein:
the second rotor includes the second convex portions in positions corresponding to at least one of 90 degrees, 120 degrees, and 180 degrees around the second rotation shaft.

11. The treatment device according to claim 1, wherein:
when the second rotor axially rotates a predetermined angle around the second rotation shaft from a neutral state in which the end effector extends straight along the longitudinal axis of the sheath, the first rotor axially rotates a predetermined angle around the first rotation shaft.

12. The treatment device according to claim 1, further comprising:
a gear mechanism that is provided between the operation handle and the second rotor and adjusts a rotation amount of the second rotor relative to a rotation amount of the operation handle.

13. The treatment device according to claim 1, further comprising:
a gear mechanism that is provided between the first rotor and the driving shaft and adjusts a movement amount of the driving shaft along the longitudinal axis relative to a rotation amount of the first rotor.

14. The treatment device according to claim 1, wherein:
the driveshaft is configured to drive between the first rotor and the end effector.

15. The treatment device according to claim 1, wherein:
the end effector includes a holding section configured to hold living tissue, and an energy output section that is provided in the holding section and applies energy to and treats living tissue held by the holding section.

16. The treatment device according to claim 1, wherein when the first rotor rotates, a rotation of the second rotor causes the first rotor to rotate, and the first rotor converts the rotation of the operation handle into a horizontal movement of the driving shaft by movement of the coupling portions.

* * * * *